(12) United States Patent
Sofranko et al.

(10) Patent No.: US 9,114,223 B2
(45) Date of Patent: Aug. 25, 2015

(54) STRAPPING FORCE INDICATOR ACCESSORY

(75) Inventors: Richard Andrew Sofranko, Finleyville, PA (US); Jerome Matula, Jr., Apollo, PA (US); Anthony Vincent Startare, Belle Vernon, PA (US); Lance Ranard Busch, Trafford, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 614 days.

(21) Appl. No.: 13/503,089

(22) PCT Filed: Sep. 28, 2010

(86) PCT No.: PCT/IB2010/054358
§ 371 (c)(1),
(2), (4) Date: Apr. 20, 2012

(87) PCT Pub. No.: WO2011/048518
PCT Pub. Date: Apr. 28, 2011

(65) Prior Publication Data
US 2012/0199131 A1    Aug. 9, 2012

Related U.S. Application Data

(60) Provisional application No. 61/254,264, filed on Oct. 23, 2009.

(51) Int. Cl.
*A61M 16/06* (2006.01)
*G01L 5/06* (2006.01)

(52) U.S. Cl.
CPC ........... *A61M 16/0683* (2013.01); *A61M 16/06* (2013.01); *G01L 5/06* (2013.01); *A61M 2205/583* (2013.01)

(58) Field of Classification Search
CPC .............. A41C 5/00; A41C 7/00; A41C 7/06; A41H 1/02; A41H 5/01; A41H 5/02; A41H 1/00; A41H 5/00; A61B 5/107; A61B 5/4312; A61B 5/022; A61B 5/02233; A61B 5/0408; A61B 5/061; A61B 5/681; G01B 3/1002; G01B 5/025; G01B 3/008; G01B 5/02; G06Q 30/0625; B66C 1/18; B66C 15/06; B66C 1/12; D07B 1/148; D07B 1/145; A61F 13/00; A61F 13/00059; A61F 13/06; A61F 13/069; A61F 13/08; A61F 13/085; A61F 5/445; A61M 16/0683; A61M 16/00; A61M 16/04; A61M 16/0488; A61M 16/0497; A61M 16/06; A61M 16/0633; A61M 16/0666; A61M 16/08; A61M 25/02; A62B 18/084; A62B 18/08; A62B 7/10; A01K 27/00; A01K 27/005; A41F 9/00; A41F 9/002; A44B 11/25; A44B 11/2561; A44B 11/2569; A44B 11/26; A44B 11/266; A44C 5/00; A44C 5/0069; B60R 22/12; B60R 22/16; B60R 22/18; B63C 11/02; B63C 11/12; B63C 1/12; B63C 1/18; B63C 15/06; D03D 11/00; G09F 3/00; G09F 7/00
USPC ......... 128/587, 869, 870, 876, 877, 878, 882, 128/206.21–207.13; 602/75, 76, 77, 60, 61, 602/201, 202, 203; 116/212, DIG. 34; 2/10, 2/416–418, 421–422, 425, 9, 410, 4–5, 2/601, 602, 7, 8, 76, 183, 195.1–195.4, 2/220–221, 237; 604/175
See application file for complete search history.

(56) References Cited

U.S. PATENT DOCUMENTS

| | | | |
|---|---|---|---|
| 3,613,679 A * | 10/1971 | Bijou | ............................... 602/75 |
| 4,617,037 A | 10/1986 | Okada | |
| 5,054,433 A * | 10/1991 | Pfleger | .......................... 119/856 |
| 5,517,986 A | 5/1996 | Starr | |
| 6,640,460 B1 * | 11/2003 | Nabarro et al. | .................. 33/759 |
| 7,422,256 B2 * | 9/2008 | Mueller | ........................... 294/74 |
| 7,938,468 B2 * | 5/2011 | Mueller | ........................... 294/74 |
| 2003/0144596 A1 | 7/2003 | Tsubata | |
| 2006/0000223 A1 | 1/2006 | Dickerson | |
| 2007/0193446 A1 | 8/2007 | Nakamura | |

| | | | | |
|---|---|---|---|---|
| 2007/0267021 A1* | 11/2007 | Kwok | | 128/206.12 |
| 2008/0083412 A1* | 4/2008 | Henry et al. | | 128/207.11 |
| 2008/0115788 A1 | 5/2008 | Eschen | | |

FOREIGN PATENT DOCUMENTS

| | | |
|---|---|---|
| EP | 1902743 A1 | 3/2008 |
| JP | 2006258302 A | 9/2006 |

\* cited by examiner

*Primary Examiner* — Annette Dixon (74) *Attorney, Agent, or Firm* — Michael W. Haas (57) ABSTRACT

An apparatus for indicating a strapping force applied by a headgear of a patient interface device. The apparatus includes a first portion structured to be selectively connectable to a connecting element of a mask of the patient interface device, a second portion structured to be selectively connectable to a strap of the headgear, and a force gauging mechanism coupled to the first portion and the second portion. The force gauging mechanism is structured to gauge and indicate a force being applied by the headgear in response to the second strap portion being pulled by the strap of the headgear.

13 Claims, 4 Drawing Sheets

STRAPPING FORCE INDICATOR ACCESSORY

CROSS-REFERENCE TO RELATED APPLICATIONS

This patent application claims the priority benefit under 35 U.S.C. §371 of international patent application no. PCT/IB2010/054358, filed Sep. 28, 2010, which claims the priority benefit under 35 U.S.C. §119(e) of U.S. Provisional Application No. 61/254,264 filed on Oct. 23, 2009, the contents of which are herein incorporated by reference.

BACKGROUND OF THE INVENTION

1. Field of the Invention

The present invention relates to patient interface devices for transporting a gas to and/or from an airway of a user, and, in particular, to an accessory for use with a headgear in a patient interface system for gauging and indicating the current strapping force applied by the headgear.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal mask that covers the nose, a nasal/oral mask that covers the nose and mouth, or full face mask that covers the patient face, on the face of a patient. The patient interface device interfaces the ventilator or pressure support device with the airway of the patient, so that a flow of breathing gas can be delivered from the pressure/flow generating device to the airway of the patient. It is known to maintain such masks on the face of a wearer by a headgear having upper and lower straps, each having opposite ends threaded through connecting elements provided on the opposite sides and top of a mask. Because such masks are typically worn for an extended period of time, it is important for the headgear to maintain the mask in a tight enough seal against a patient's face without discomfort. One such headgear is disclosed in U.S. Pat. No. 5,517,986, which is assigned to the assignee of the present application, and includes a cap-like headpiece adapted to fit the crown and back of a patient's head and lower straps for providing a two-point connection with a gas delivery mask.

Over tightening of mask headgear straps frequently occurs during therapy such as OSA therapy. Over tightening is undesirable as it typically causes discomfort, facial red marks, pressure sores and/or open wounds. As a result, over tightening can have a tremendously negative effect on compliance with therapy as patients will be reluctant to use the mask as often and/or for as long as directed. The importance of therapy compliance is increasing, as insurance and Medicare guidelines are now requiring the industry to prove compliance for their patient populations.

In the clinical setting, an experienced technician or therapist may be knowledgeable enough to avoid unnecessary over tightening. However, it is often the case that even such experienced caregivers over tighten headgear and/or directly or indirectly instruct the patient to over tighten in order to ensure that a good seal is achieved so that therapy, such as CPAP therapy, is delivered.

In addition, as mask designs evolve, the amount of strapping force needed to obtain a good seal between the mask and the patient's face often decreases. However, a patient using such a mask may not know or understand that less strapping force (i.e., than was required for prior mask designs) is needed. This lack of understanding may lead to over tightening of the headgear used in conjunction with the mask.

Thus, there is a need for a solution that helps patients to avoid unnecessary over tightening of headgear while at the same time ensuring that proper therapy is delivered.

SUMMARY OF THE INVENTION

In one embodiment, an apparatus is provided for indicating a strapping force applied by a headgear of a patient interface device that is used as an accessory in conjunction with a headgear strap. The apparatus includes a first portion structured to be selectively connectable to a connecting element of a mask of the patient interface device, a second portion structured to be selectively connectable to a strap of the headgear, and a force gauging mechanism coupled to the first portion and the second portion. The force gauging mechanism is structured to gauge and indicate a force being applied by the headgear in response to the second strap portion being pulled by the strap of the headgear. The user can place the force measurement accessory in series with the headgear strap to determine a proper strapping force, then remove the force measurement accessory from the strap so that it does not impede with the normal use of the mask, such as during sleep.

In one particular embodiment, the first portion includes a first strap portion and the second portion includes a second strap portion, and the force gauging mechanism is structured to gauge and indicate the force being applied by the headgear in response to the second strap portion being stretched. The first strap portion preferably includes a fastening system for connecting the first strap portion to the connecting element, and the second strap portion preferably includes a second connecting element for connecting the second strap element to a second fastening system of the strap of the headgear. Each fastening system may be a hook and loop fastener system.

In another particular embodiment, the force gauging mechanism includes a sheath element coupled to the second strap portion at a first position, wherein the second strap portion is free to stretch within the sheath element from the first position in a longitudinal direction along a length of the second strap portion. The second strap portion preferably includes at least one indicium on a surface thereof, and the sheath element includes at least one window, wherein one or more of the indicium/indicia is structured to be visible through the at least one window when the second strap portion is being stretched in the longitudinal direction.

In one embodiment, the at least one window is a single window and the at least one indicium is a plurality of indicia, such as a plurality of numbers or a plurality of indicator strips. In another embodiment, the at least one window is a single window having a plurality of indicator marks positioned adjacent thereto on a top surface of the sheath element, and the at least one indicium is an indicator strip, an indicator block, or an indicator strip positioned adjacent to an indicator block. In still another embodiment, the at least one window is a plurality of windows positioned along a length of the sheath element. In this embodiment, the at least one indicium may be an indicator strip, wherein the windows are positioned so that the indicator strip is visible through only one of the windows at a time as the second strap portion is being stretched in the longitudinal direction.

Alternatively, the at least one indicium is a plurality of indicia, wherein the windows and the indicia are positioned so that each of the indicia is visible through only certain ones of the windows as the second strap portion is being stretched in the longitudinal direction. In still another embodiment, the second strap portion includes a hole, and the sheath element includes (i) a window having a plurality of indicator marks positioned adjacent thereto on a top surface of the sheath element and (ii) an internal back wall of a first color. The first color is visible through the hole and the window when the second strap portion is being stretched in the longitudinal direction.

Also provided is a method for indicating a strapping force applied by a headgear of a patient interface device that includes releasably connecting a first portion of an indicator apparatus to a connecting element of a mask of the patient interface device, releasably connecting a second portion of the indicator apparatus to a strap of the headgear, and gauging and indicating on the indicator apparatus a force being applied by the headgear in response to the second strap portion being pulled by the strap of the headgear.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
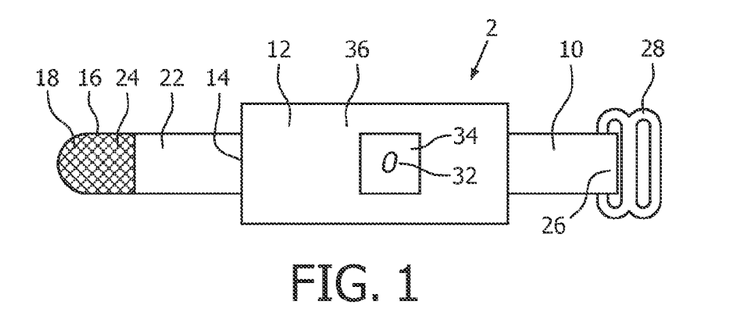
FIGS. 1 and 2 are top plan and side views, respectively, of a strapping force gauging device according to one embodiment of the present invention.
Figure 2:
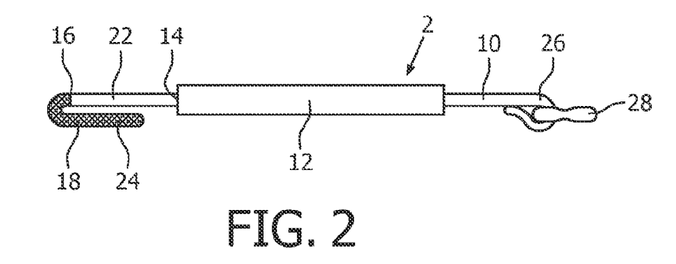
Figure 4:
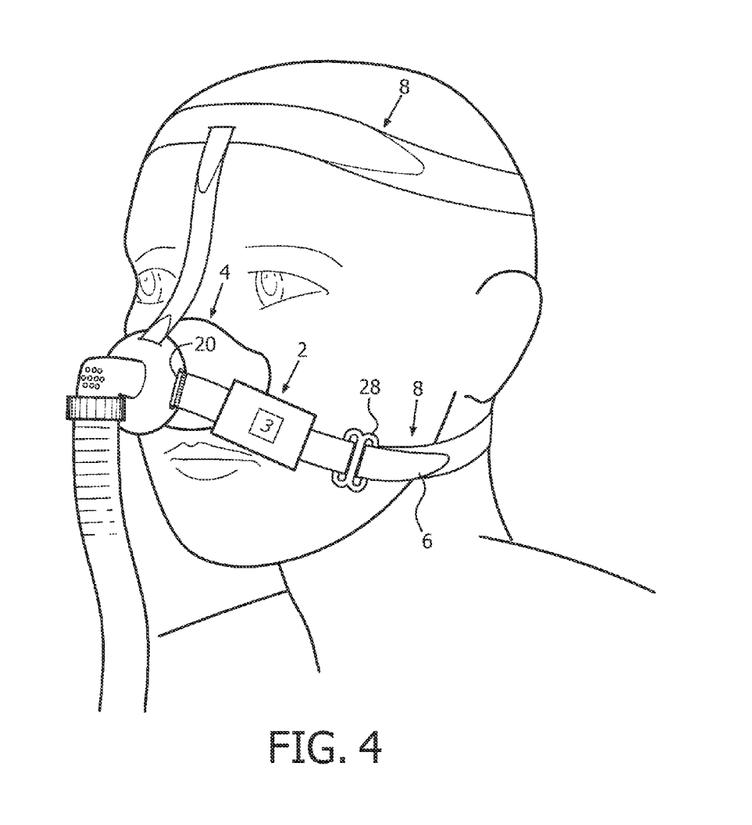
FIG. 4 is a schematic diagram showing the strapping force gauging device of FIGS. 1 and 2 being used in conjunction with one particular exemplary patient interface device.

FIGS. 1 and 2 are top plan and side views, respectively, of strapping force gauging device or accessory 2 according to one embodiment of the present invention. As illustrated in FIG. 4, and described in greater detail below, strapping force gauging device 2 is an accessory piece structured to be inserted in between patient interface device 4, such as a nasal mask, and strap 6 (e.g., a lower strap) of headgear 8. As an accessory, it can be readily placed in series with the headgear strap, used to measure the force, and then removed, so that the user need not sleep, for example, with the force measurement device coupled to the headgear strap. Strapping force gauging device 2 is structured to provide a visual indication of a current strapping force of headgear 8 to help the patient apply an appropriate strapping force via headgear 8 and to discourage/help to avoid over tightening of headgear 8. Although a nasal mask is shown in FIG. 4, it should be understood that that is meant to be exemplary only and that the present invention may be employed in conjunction with a variety of types of patient interface devices, including, without limitation, nasal/oral masks and full face masks.

Strapping force gauging device 2 includes strap element 10 made of an elastic material, such as silicone, polyurethane, woven fabric, plastic elastomer, or rubber, to allow it to stretch when a longitudinal force (along the length of strap element 10) is applied thereto. Strapping force gauging device 2 also includes sheath element 12 through which strap element 10 is inserted such that sheath 12 encases a portion of strap element 10. Sheath element 12 is made of an in-elastic material, such as woven or non-woven fabric, a thermoplastic material, a Thermoset material, leather, metal, ceramic, or glass, such that sheath element 12 is not permitted to stretch when a longitudinal force resulting from adjustment of headgear 8 is applied thereto.

Figure 3:
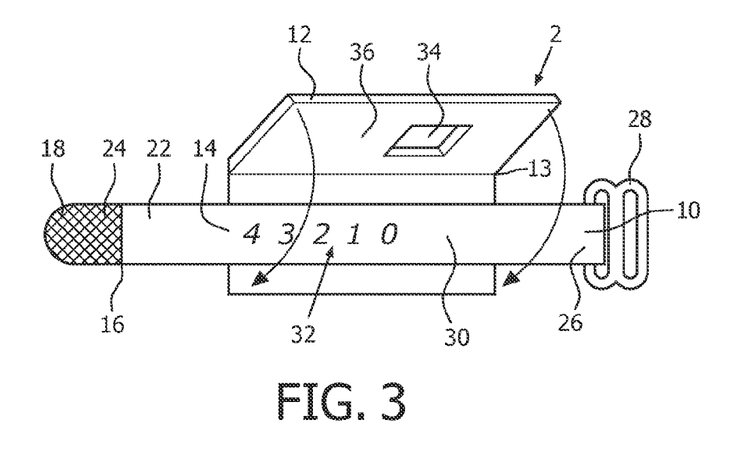
FIG. 3 is a diagram of the strapping force gauging device of FIGS. 1 and 2 showing how the sheath element thereof is attached to the strap element thereof.

Sheath element 12 is affixed to strap element 10 at position 14 on strap element 10 by, for example and without limitation, an adhesive, a hook and loop fastening system, such as VEL-CRO®, or any other suitable fastening element/system. As a result, strap element 10 is able to move and stretch longitudinally relative to sheath element 12 from position 14 (in a rightward direction in FIG. 1) when a longitudinal force is applied along the length of strap element 10. As shown in FIG. 3, in the presently illustrated embodiment, sheath element 12 is able to be bent at hinge portion 13 to enable it to be closed over strap element 10. Sheath element 12 is then held in a closed condition in which it encases a portion of strap element 10 as described above as a result of the affixation at position 14. An adhesive or other similar mechanism may also be used at a position on sheath element 12 that is opposite hinge portion 13 in order to assist in holding sheath element 12 closed.

First end 16 of strap element 10 includes fastening system 18 for enabling strap element 10, and thus strapping force gauging device 2, to be selectively and releasably attached to connecting element 20 of patient interface device 4 (FIG. 4). In the illustrated embodiment, fastening system 18 is a hook and loop fastener, such as VELCRO®. More specifically, in this embodiment, the exterior of strap element 10 includes a loop fastener portion 22. A corresponding hook fastener portion 24 is provided on first end 16. Thus, first end 16 may be threaded through the elongated opening of connecting element 20 and then bent back on itself to adhere hook fastener portion 24 to loop fastener portion 22. Of course, the present invention contemplates that first end 16 of strap element 10 can use other forms of connection other than hook and loop fasteners such as snaps or buckles.

In addition, second end 26 of strap element 10 has connecting element 28 attached thereto to enable a fastening system forming part of strap 6 of headgear 8 to be selectively and releasably attached to strapping force gauging device 2 via connecting element 28 (FIG. 4). In the illustrated embodiment, the fastening system forming part of strap 6 is a hook and loop fastener, such as VELCRO®, and is similar to fastening system 18 described above. In particular, the end of strap 6 is adapted to be brought forward from a rear joining piece (not shown) of headgear 8 beneath the patient's ear and threaded through connecting element 28. The end tab portion of strap 6 is bent back to adhere to the exterior loop fastener portion provided as part of strap 6. Of course, the present invention contemplates that other forms of connection other than hook and loop fasteners such as snaps or buckles may be employed to enable strap 6 to be selectively and releasably attached to strapping force gauging device 2.

Referring to FIG. 3, central portion 30 of strap element 10 is provided with indicia 32 along the length thereof. In the embodiment shown, each indicium 32 is a number (0, 1, 2, 3, 4). In addition, window 34 is provided in top surface 36 of sheath element 12 to enable indicia 32 to be seen through window 34 as strap element 10 is stretched.

In operation, strapping force gauging device 2 is inserted between patient interface device 4 and strap 6 of headgear 8 as shown in FIG. 4. Indicia 32 are positioned on central portion 30 of strap element 10 and strap element 10 is calibrated such that each indicium 32 represents a particular level of strapping force as strap 6 is pulled and fastened by the patient. The patient may be instructed as to which indicium 32 represents an appropriate strapping force for that patient so that over tightening of headgear 8 can be avoided. Specifically, in the embodiment shown in FIGS. 1-4, the patient will know that if, when tightening headgear 8 by pulling on strap 6, a number higher than a certain predetermined number is showing through window 34, headgear 8 has been over tightened and should be adjusted so that less strapping force is applied.

It should be understood that while strapping force gauging device 2 is shown in FIG. 4 as being inserted between patient interface device 4 and strap 6 which is a lower strap, strapping force gauging device 2 may be used in conjunction with other straps provided in other locations. In addition, more than one strapping force gauging device 2 may be used with a particular headgear (i.e., one may be used with each strap thereof if desired).

Figure 5:
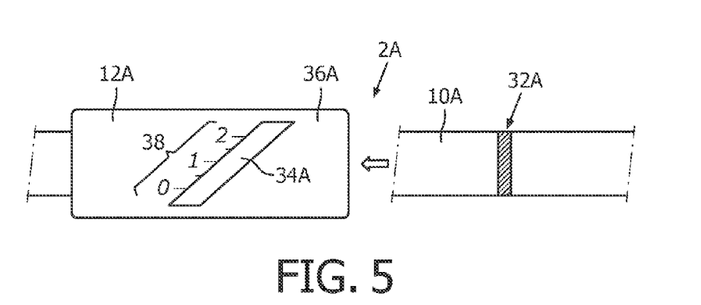
FIGS. 5-11 are schematic illustrations of selected portions of strapping force gauging devices according to various alternative embodiments of the present invention.

FIG. 5 is a schematic illustration of selected portions of strapping force gauging device 2A according to an alternative embodiment of the present invention. Strapping force gauging device 2A includes strap element 10A (similar to strap element 10) that includes indicium 32A thereon in the form of an indicator stripe. In addition, strapping force gauging device 2A includes sheath element 12A (similar to sheath element 12) that includes angled window 34A having indicator marks 38 provided adjacent thereto on top surface 36A along the length of angled window 34A. Indicator marks 38 are positioned along angled window 34A and strap element 10A is calibrated such that the indicator mark 38 next to which and below which indicium 32A is positioned as strap 6 is pulled and fastened by the patient represents a particular level of strapping force. The patient may be instructed as to which indicator mark 38 represents an appropriate strapping force for that patient so that over tightening of headgear 8 can be avoided. Specifically, in the embodiment shown in FIG. 5, the patient will know that if, when tightening headgear 8 by pulling on strap 6, indicium 32A is next to and below a number higher than a certain predetermined number, headgear 8 has been over tightened and should be adjusted so that less strapping force is applied.

Figure 6:
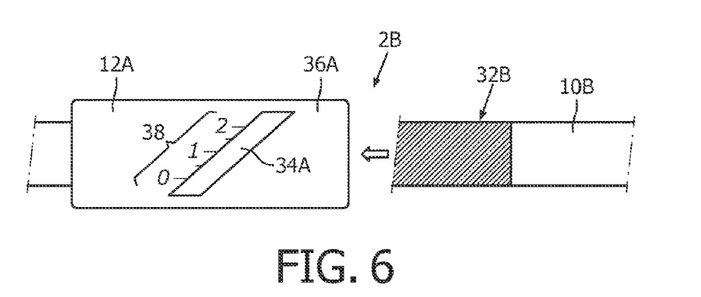

FIG. 6 is a schematic illustration of selected portions of strapping force gauging device 2B according to a further alternative embodiment of the present invention. Strapping force gauging device 2B is similar to strapping force gauging device 2A, except that it includes strap element 10B (similar to strap element 10) that includes indicium 32B thereon in the form of a solid indicator block. In this embodiment, the end of the solid indicator block will be positioned next to and below indicator marks 38 as strap element 10B is stretched.

Figure 7:
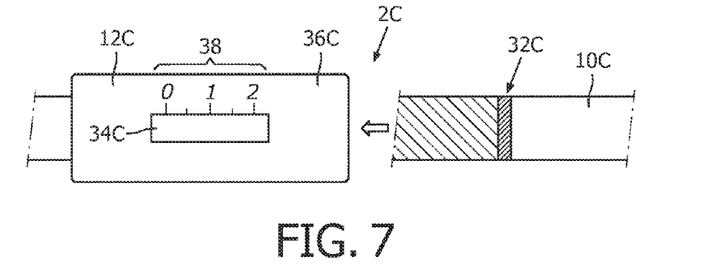

FIG. 7 is a schematic illustration of selected portions of strapping force gauging device 2C according to another alternative embodiment of the present invention. Strapping force gauging device 2C is similar to strapping force gauging devices 2A and 2B, except that it includes (i) sheath element 12C (similar to sheath element 12) that includes horizontal window 34C having indicator marks 38 provided adjacent thereto on top surface 36C along the length of horizontal window 34C, and (ii) strap element 10C (similar to strap element 10) that includes indicium 32C thereon in the form of a solid indicator block directly adjacent to an indicator stripe. In this embodiment, the indicator stripe will be positioned below indicator marks 38 as strap element 10C is stretched.

Figure 8:
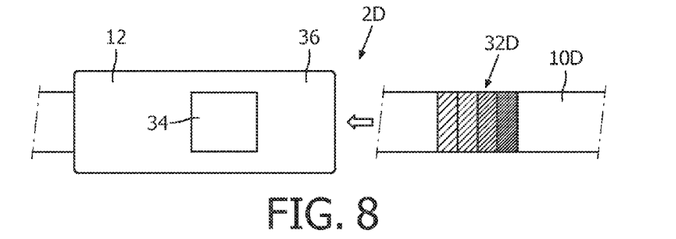

FIG. 8 is a schematic illustration of selected portions of strapping force gauging device 2D according to another alternative embodiment of the present invention. Strapping force gauging device 2D includes sheath element 12 (FIG. 1) and strap element 10D (similar to strap element 10) that includes indicia 32D thereon in the form of a plurality of adjacent, differently colored indicator stripes. The indicator stripes forming the indicia 32D are positioned along strap element 10D and strap element 10D is calibrated such that the particular indicator stripe or stripes seen through window 34 as strap 6 is pulled and fastened by the patient represent a particular level of strapping force. The patient may be instructed as to which color indicator stripe or stripes represent an appropriate strapping force for that patient so that over tightening of headgear 8 can be avoided. Specifically, in the embodiment shown in FIG. 8, the patient will know that if, when tightening headgear 8 by pulling on strap 6, a particular color indicator stripe can be seen through window 34, headgear 8 has been over tightened and should be adjusted so that less strapping force is applied.

Figure 9:
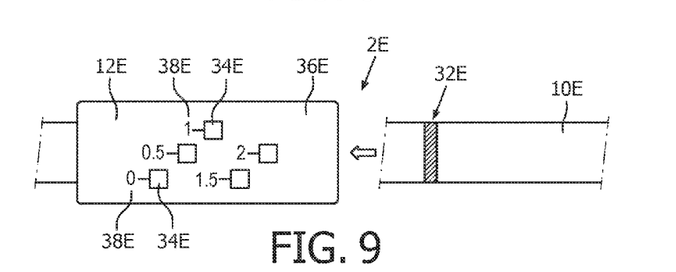

FIG. 9 is a schematic illustration of selected portions of strapping force gauging device 2E according to yet another alternative embodiment of the present invention. Strapping force gauging device 2E includes strap element 10E (similar to strap element 10) that includes indicium 32E thereon in the form of an indicator stripe. In addition, strapping force gauging device 2E includes sheath element 12E (similar to sheath element 12) that includes a plurality of windows 34E each having an indicator mark 38E provided adjacent thereto on top surface 36E. The windows 34E are positioned along top surface 36E of sheath element 12E and strap element 10E is calibrated such that the particular window 34E through which the indicator stripe is seen as strap 6 is pulled and fastened by the patient represents a particular level of strapping force. The patient may be instructed as to which window 34E represents an appropriate strapping force for that patient so that over tightening of headgear 8 can be avoided. Specifically, in the embodiment shown in FIG. 9, the patient will know that if, when tightening headgear 8 by pulling on strap 6, the indicator stripe can be seen through a particular window or windows 34E, headgear 8 has been over tightened and should be adjusted so that less strapping force is applied.

Figure 10:
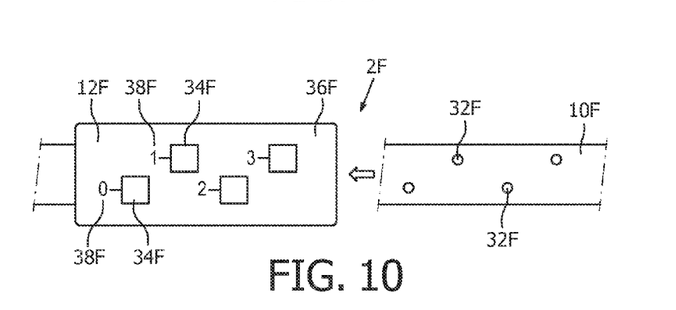

FIG. 10 is a schematic illustration of selected portions of strapping force gauging device 2F according to yet another alternative embodiment of the present invention. Strapping force gauging device 2F includes strap element 1 OF (similar to strap element 10) that includes indicia 32F thereon in the form of a plurality of indicator dots. In addition, strapping force gauging device 2F includes sheath element 12F (similar to sheath element 12) that includes a plurality of windows 34F each having an indicator mark 38F provided adjacent thereto on top surface 36F. As strap 10F is stretched, only one window 34F at a time will have an indicator dot visible therethrough. The windows 34F are positioned along top surface 36F of sheath element 12F and strap element 10F is calibrated such that the particular window 34F through which an indicator dot can be seen as strap 6 is pulled and fastened by the patient represents a particular level of strapping force. The patient may be instructed as to which window 34F represents an appropriate strapping force for that patient so that over tightening of headgear 8 can be avoided. Specifically, in the embodiment shown in FIG. 10, the patient will know that if, when tightening headgear 8 by pulling on strap 6, an indicator dot can be seen through a particular window or windows 34F, headgear 8 has been over tightened and should be adjusted so that less strapping force is applied.

Figure 11:
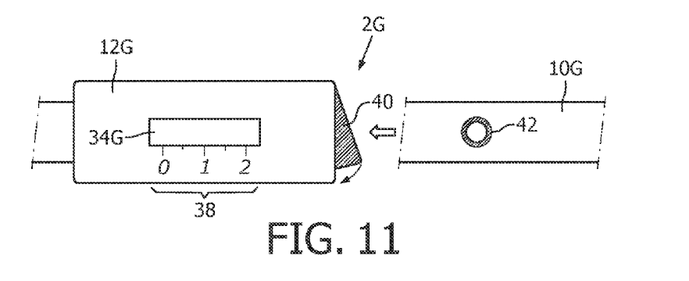

FIG. 11 is a schematic illustration of selected portions of strapping force gauging device 2G according to another alternative embodiment of the present invention. Strapping force gauging device 2G includes sheath element 12G (similar to sheath element 12) that includes horizontal window 34C having indicator marks 38 provided adjacent thereto on top surface 36C along the length of horizontal window 34C. In addition, sheath element 12G includes internal back wall 40 that is colored a different color than strap element 10G (e.g., a neon or other bright color). Strapping force gauging device 2G strap element 10G (similar to strap element 10) that includes reinforced hole 42 therein that is structured to allow the color of internal back wall 40 to show therethrough as strap element 10G moves relative to sheath element 12G.

In this embodiment, reinforced hole 42 (and the color showing through it) will be positioned above indicator marks 38 as strap element 10G is stretched. Indicator marks 38 are positioned along horizontal window 34G and strap element 10G is calibrated such that the indicator mark 38 above which reinforced hole 42 (and the color showing through it) is positioned as strap 6 is pulled and fastened by the patient represents a particular level of strapping force. The patient may be instructed as to which indicator mark 38 represents an appropriate strapping force for that patient so that over tightening of headgear 8 can be avoided. Specifically, in the embodiment shown in FIG. 11, the patient will know that if, when tightening headgear 8 by pulling on strap 6, reinforced hole 42 (and the color showing through it) is above a number higher than a certain predetermined number, headgear 8 has been over tightened and should be adjusted so that less strapping force is applied.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus for indicating a strapping force applied by a headgear of a patient interface device, comprising:
   a first portion structured to be selectively connectable to a connecting element of a mask of the patient interface device, the first portion including a first strap portion;
   a second portion structured to be selectively connectable to a strap of the headgear, the second portion including a second strap portion; and
   a force gauging mechanism coupled to the first portion and the second portion, the force gauging mechanism being structured to gauge and indicate a force being applied by the headgear in response to the second strap portion being pulled by the strap of the headgear, wherein the force gauging mechanism comprises a sheath element coupled to the second strap portion at a first position, wherein the second strap portion is free to stretch within the sheath element from the first position in a longitudinal direction along a length of the second strap portion, wherein the second strap portion includes at least one indicium on a surface thereof, wherein the sheath element includes a plurality of windows positioned along a length of the sheath element, and wherein one or more of the at least one indicium is structured to be visible through one or more of the windows when the second strap portion is being stretched in the longitudinal direction.

2. The apparatus according to claim 1, wherein the first strap portion includes a fastening system for connecting the first strap portion to the connecting element, and wherein the second strap portion includes a second connecting element for connecting the second strap element to a second fastening system of the strap of the headgear.

3. The apparatus according to claim 2, wherein the fastening system and the second fastening system each comprise a hook and loop fastener system.

4. The apparatus according to claim 3, wherein the at least one indicium is a plurality of indicia.

5. The apparatus according to claim 1, wherein the at least one indicium is an indicator strip, wherein the windows are positioned so that the indicator strip is visible through only one of the windows at a time as the second strap portion is being stretched in the longitudinal direction.

6. The apparatus according to claim 1, wherein the at least one indicium is a plurality of indicia, wherein the windows and the indicia are positioned so that each of the indicia is visible through only certain ones of the windows as the second strap portion is being stretched in the longitudinal direction.

7. A method for indicating a strapping force applied by a headgear of a patient interface device, comprising:
   releasably connecting a first portion of an indicator apparatus to a connecting element of a mask of the patient interface device, wherein the first portion comprises a first strap portion;
   releasably connecting a second portion of the indicator apparatus to a strap of the headgear, wherein the second portion comprises a second strap portion, wherein the indicator apparatus includes a force gauging mechanism coupled to the first portion and the second portion, wherein the force gauging mechanism comprises a sheath element coupled to the second strap portion at a first position, wherein the second strap portion is free to stretch within the sheath element from the first position in a longitudinal direction along a length of the second strap portion, wherein the second strap portion includes at least one indicium on a surface thereof, wherein the sheath element includes a plurality of windows positioned along a length of the sheath element, and wherein one or more of the at least one indicium is structured to be visible through one or more of the windows when the second strap portion is being stretched in the longitudinal direction; and gauging and indicating on the indicator apparatus a force being applied by the headgear in response to the second strap portion being pulled by the strap of the headgear.

8. A method for indicating a strapping force applied by a headgear of a patient interface device, comprising:

releasably connecting a first portion of an indicator apparatus to a connecting element of a mask of the patient interface device, wherein the first portion comprises a first strap portion;

releasably connecting a second portion of the indicator apparatus to a strap of the headgear, wherein the second portion comprises a second strap portion, wherein the indicator apparatus includes a force gauging mechanism coupled to the first portion and the second portion, wherein the force gauging mechanism comprises a sheath element coupled to the second strap portion at a first position, wherein the second strap portion is free to stretch within the sheath element from the first position in a longitudinal direction along a length of the second strap portion, wherein the second strap portion includes at least one indicium on a surface thereof, wherein the sheath element includes a single window positioned along a length of the sheath element, wherein the single window has a plurality of indicator marks positioned adjacent thereto on a top surface of the sheath element, and wherein one or more of the at least one indicium is structured to be visible through the single window when the second strap portion is being stretched in the longitudinal direction; and gauging and indicating on the indicator apparatus a force being applied by the headgear in response to the second strap portion being pulled by the strap of the headgear.

9. The method according to claim 7, further comprising detaching the first portion from the connecting element of a mask of the patient interface device and the second portion from the strap following the gauging and indicating step.

10. An apparatus for indicating a strapping force applied by a headgear of a patient interface device, comprising:

a first portion structured to be selectively connectable to a connecting element of a mask of the patient interface device, the first portion including a first strap portion;

a second portion structured to be selectively connectable to a strap of the headgear, the second portion including a second strap portion; and a force gauging mechanism coupled to the first portion and the second portion, the force gauging mechanism being structured to gauge and indicate a force being applied by the headgear in response to the second strap portion being pulled by the strap of the headgear, wherein the force gauging mechanism comprises a sheath element coupled to the second strap portion at a first position, wherein the second strap portion is free to stretch within the sheath element from the first position in a longitudinal direction along a length of the second strap portion, wherein the second strap portion includes at least one indicium on a surface thereof, wherein the sheath element includes a single window positioned along a length of the sheath element, wherein the single window has a plurality of indicator marks positioned adjacent thereto on a top surface of the sheath element, and wherein one or more of the at least one indicium is structured to be visible through the single window when the second strap portion is being stretched in the longitudinal direction.

11. The apparatus according to claim 10, wherein the first strap portion includes a fastening system for connecting the first strap portion to the connecting element, and wherein the second strap portion includes a second connecting element for connecting the second strap element to a second fastening system of the strap of the headgear.

12. The apparatus according to claim 10, wherein the at least one indicium is an indicator strip, an indicator block, or an indicator strip positioned adjacent to an indicator block.

13. The apparatus according to claim 10, wherein the second strap portion includes a hole, wherein the sheath element includes an internal back wall of a first color, wherein the first color is visible through the hole and the single window when the second strap portion is being stretched in the longitudinal direction.

* * * * *